US012605128B2

(12) United States Patent
Wang et al.

(10) Patent No.: US 12,605,128 B2
(45) Date of Patent: Apr. 21, 2026

(54) X-RAY DETECTOR IN PATIENT BED

(71) Applicant: CARESTREAM HEALTH, INC.,
Rochester, NY (US)

(72) Inventors: Xiaohui Wang, Pittsford, NY (US);
Robert S. Jones, Rochester, NY (US);
Weidong Huang, Fairport, NY (US);
David H. Foos, Webster, NY (US)

(73) Assignee: Carestream Health, Inc., Rochester,
NY (US)

( * ) Notice: Subject to any disclaimer, the term of this
patent is extended or adjusted under 35
U.S.C. 154(b) by 106 days.

(21) Appl. No.: 18/556,738

(22) PCT Filed: Jun. 20, 2022

(86) PCT No.: PCT/US2022/034146
§ 371 (c)(1),
(2) Date: Oct. 23, 2023

(87) PCT Pub. No.: WO2022/271583
PCT Pub. Date: Dec. 29, 2022

(65) Prior Publication Data
US 2024/0197270 A1     Jun. 20, 2024

Related U.S. Application Data

(60) Provisional application No. 63/214,287, filed on Jun.
24, 2021.

(51) Int. Cl.
A61B 6/42 (2024.01)
A61B 6/00 (2006.01)
(Continued)

(52) U.S. Cl.
CPC .............. A61B 6/42 (2013.01); A61B 6/0407
(2013.01); A61B 6/4417 (2013.01); A61B
6/463 (2013.01); A61B 6/5247 (2013.01);
A61B 6/547 (2013.01)

(58) Field of Classification Search
CPC ....... A61B 6/42; A61B 6/0407; A61B 6/4417;
A61B 6/463; A61B 6/5247; A61B 6/547;
A61B 6/4452; A61B 6/4283
See application file for complete search history.

(56) References Cited

U.S. PATENT DOCUMENTS

| | | | |
|---|---|---|---|
| 2002/0065461 A1* | 5/2002 | Cosman .................... | G06T 7/73 |
| | | | 600/429 |
| 2007/0242806 A1 | 10/2007 | Borgmann et al. | |
| 2013/0281843 A1* | 10/2013 | Toniolo ................ | A61B 6/4452 |
| | | | 600/425 |

FOREIGN PATENT DOCUMENTS

| | | |
|---|---|---|
| EP | 1 280 004 A1 | 1/2003 |
| EP | 2 684 522 A1 | 1/2014 |
| EP | 3 320 842 A1 | 5/2018 |

OTHER PUBLICATIONS

International Search Report mailed on Oct. 17, 2022 for International Application No. PCT/US2022/034146, 3 pages.

* cited by examiner

*Primary Examiner* — Kiho Kim
(74) *Attorney, Agent, or Firm* — Eugene I Shkurko

(57) ABSTRACT

A radiographic imaging system provides a digital x-ray detector embedded in a patient bed. A patient lying normally on the bed either flat or at an angle, is positioned above the digital detector. A frame assembly is attached to the bed under the patient and movably secures the digital detector. The frame assembly includes motorized control configured to move the digital detector in the x-y plane of the detector according to commands transmitted by system operators or by automatic system instruction.

17 Claims, 4 Drawing Sheets

(51) Int. Cl.
    *A61B 6/04*            (2006.01)
    *A61B 6/46*            (2024.01)

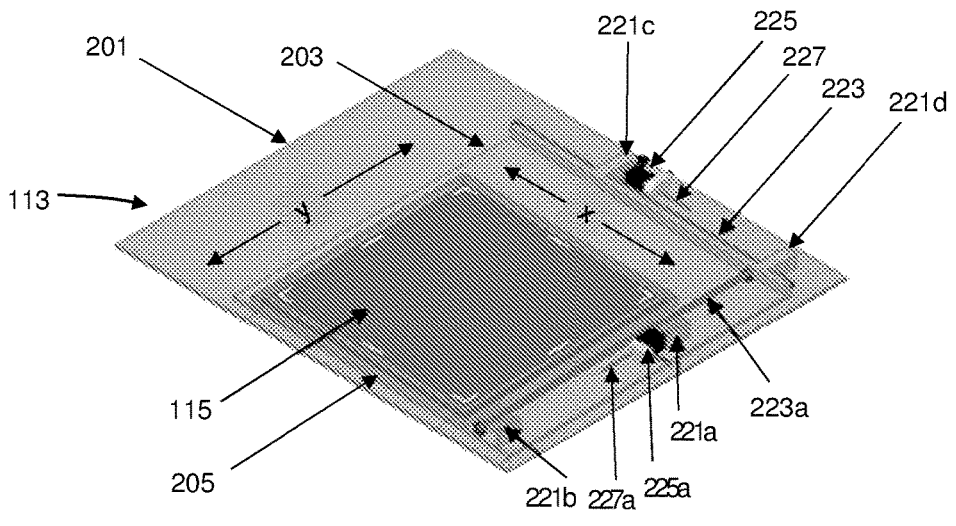
FIG. 2A
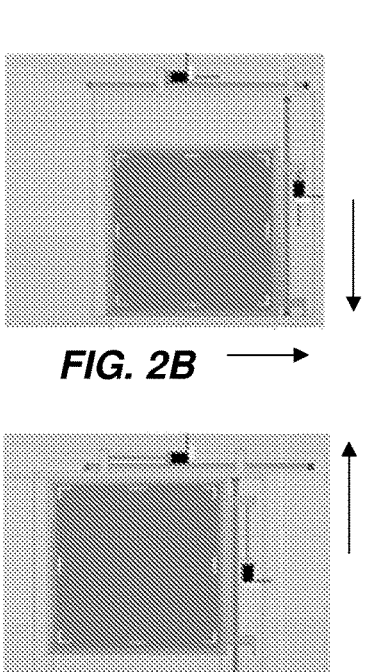
FIG. 2B
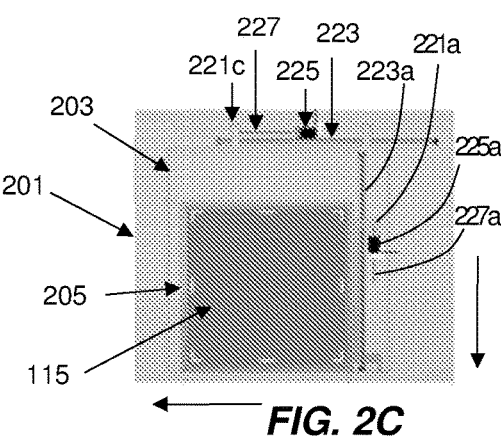
FIG. 2C
FIG. 2D
FIG. 2E

X-RAY DETECTOR IN PATIENT BED

CROSS REFERENCE TO RELATED APPLICATIONS

This application claims the benefit of and is a U.S. National Phase filing of PCT Application PCT/US2022/034146 filed Jun. 20, 2022 entitled "X- RAY DETECTOR IN PATIENT BED", in the name of Wang et al., which claims benefit of U.S. Patent Application Ser. No. 63/214, 287, filed Jun. 24, 2021, in the name of Wang et al., and entitled "X-RAY DETECTOR DEPLOYED IN PATIENT BED.

BACKGROUND OF THE INVENTION

The subject matter disclosed herein relates to medical digital x-ray imaging. Infection control has emerged as being among the most critically important factors in health-care delivery as a result of the global propagation of Covid 19. One consequence of the pandemic is that it has precipi-tated and accelerated the innovation process in a multitude of healthcare product arenas, including in areas such as personal protective equipment, ventilators, assays for Covid 19 testing, antimicrobials, among many others. In this regard, of great interest is how to build better infection control into the medical imaging process and, in particular, in the context of remote X-ray imaging of patients in intensive care units and in emergency departments. A current shift in the ICU imaging process now does not involve transporting and positioning of mobile x-ray units for imag-ing, thereby allowing patients afflicted with infectious dis-ease to remain in isolation from staff that would normally perform the imaging at the patient bedside. One difficulty in bedside patient contact is the placement and removal of an x-ray detector behind the patient for imaging.

The discussion above is merely provided for general background information and is not intended to be used as an aid in determining the scope of the claimed subject matter.

BRIEF DESCRIPTION OF THE INVENTION

It would be greatly advantageous to provide a visual indication, such as in a live digital display, to illustrate where the detector is positioned relative to the patient. One approach may use a detector that remains inside the patient's bed behind and/or below the patient for x-ray imaging when needed, and at the same time provides a visual indication through a live video image overlay displayed on a digital display panel to indicate the detector's location relative to the bed and patient.

One system disclosed herein makes use of several key enabling components. First, the detector, which may be a wireless digital detector for wirelessly transmitting captured digital x-ray images, is attached to a frame assembly that moves the detector in x and y directions, as desired, within the frame via motorized control. The frame assembly is attached to and aligned to the backboard of the bed behind the upper or lower region of a torso of the patient. The patient may be lying on the bed either in a supine position, or partially elevated at an angle. Second, one or more digital encoders may be deployed in the frame assembly to sense and electronically transmit the precise x-y location of the detector within the frame and relative to the patient bed using the known location of the frame in relation to the patient bed. Third, a video camera above the patient may be used to capture and transmit a live image of both the patient and part of the patient bed to a digital display. A processing system digitally connected to the detector, the frame assem-bly and the digital display may be used to process the encoder data and frame location to determine a position of the detector in relation to the bed. Fourth, a graphic cursor, the precise location of which is determined by the process-ing system using the encoder data together with the known location of the frame with respect to the patient bed, is visibly overlaid by the processing system onto the video display to illustrate the location and shape of the detector placed inside the patient bed. The graphic cursor overlay may be shaped as a rectangle or other useful highlighted area to indicate the location of the detector. The operator may rely on the graphic overlay in the video while using mechanical controls directly connected to the detector's frame assembly to move and adjust the detector's x-y location in the frame assembly such that the detector can be centered behind the desired patient anatomy for radiographic imaging.

In one embodiment, artificial intelligence software can be used to analyze the video stream and identify the location of the patient anatomy, e.g. chest, relative to the patient's bed, and then automatically command the movement of the detector within the frame assembly such that the detector position is appropriately centered behind the patient. Instead of using a video camera, sensors (ultrasound, infrared, radio wave, etc.) in the bed can also be deployed to sense the patient torso location and then automatically command the detector to be centered relative to the patient anatomy. X-ray exposure can be initiated remotely, i.e., outside the ICU room, in order to separate hospital staff from the patient to maximize the protection of the hospital staff from any infectious disease. Post acquisition images may also be provided for review remotely or outside the ICU room on a networked display.

A radiographic imaging system provides a digital x-ray detector embedded in a patient bed. A patient lying normally on the bed, either flat or at an angle, is positioned above the digital detector. A frame assembly is attached to the bed behind the patient and movably secures the digital detector. The frame assembly includes motorized control configured to move the digital detector in the x-y plane of the assembly according to commands transmitted by system operators or by automatic system instruction. An advantage that may be realized in the practice of some disclosed embodiments of the embedded digital detector is improved staff isolation from contagious patients.

In one embodiment, a radiography imaging system includes a patient bed having a frame assembly attached to the bed behind the patient. The frame assembly secures a digital detector and is configured to move the digital detector to a desired location within the frame assembly.

In one embodiment a method includes providing a bed for supporting a patient and attaching a frame assembly to the bed under the patient. A digital radiographic detector is attached to the the the frame assembly which is used to move the digital radiographic detector, in a plane of the detector, under the patient to a desired location.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifica-tions may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 2A is a perspective view of the detector frame assembly of the present invention, and FIGS. 2B-2E illustrate exemplary movements of the detector in the detector frame assembly;

DETAILED DESCRIPTION OF THE INVENTION

This application claims priority to U.S. Patent Application Ser. No. 63/214,287, filed Jun. 24, 2021, in the name of Wang, et al., and entitled X-RAY DETECTOR DEPLOYED IN PATIENT BED, which is hereby incorporated by reference herein in its entirety.

This application is related in certain respects to International Application Publication WO 2022/087047 A1 filed Oct. 20, 2021, in the name of Damany et al., and entitled REMOTE AND AUTOMATED INTENSIVE CARE UNIT; and U.S. patent application Ser. No. 17/666,848, filed Feb. 8, 2022, in the name of Wang et al., and entitled X-RAY BED, both of which are hereby incorporated by reference herein in their entirety.

Figure 1:
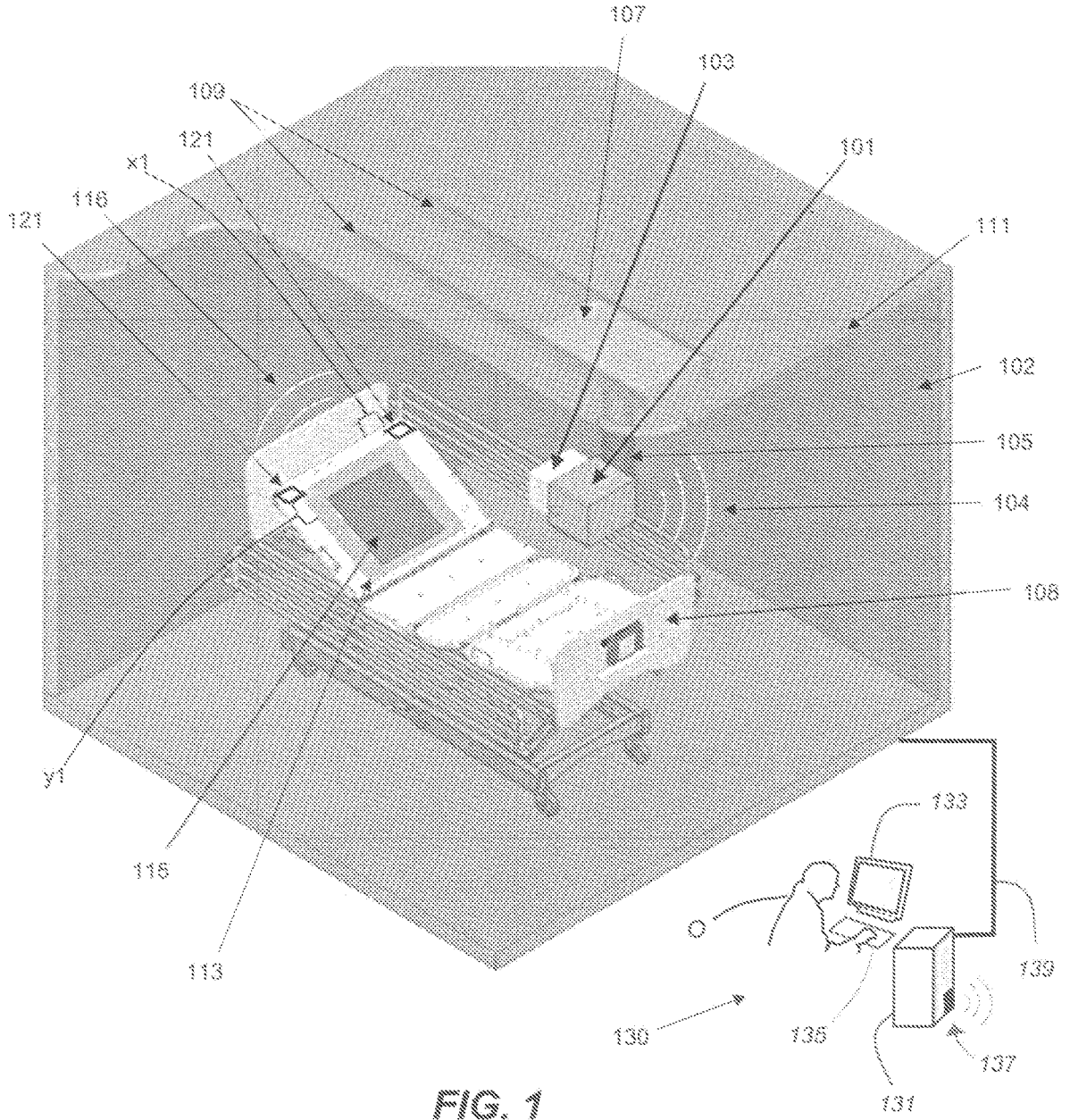
FIG. 1 is a perspective view of an exemplary medical facility including the radiographic imaging system of the present invention.
Figure 3:
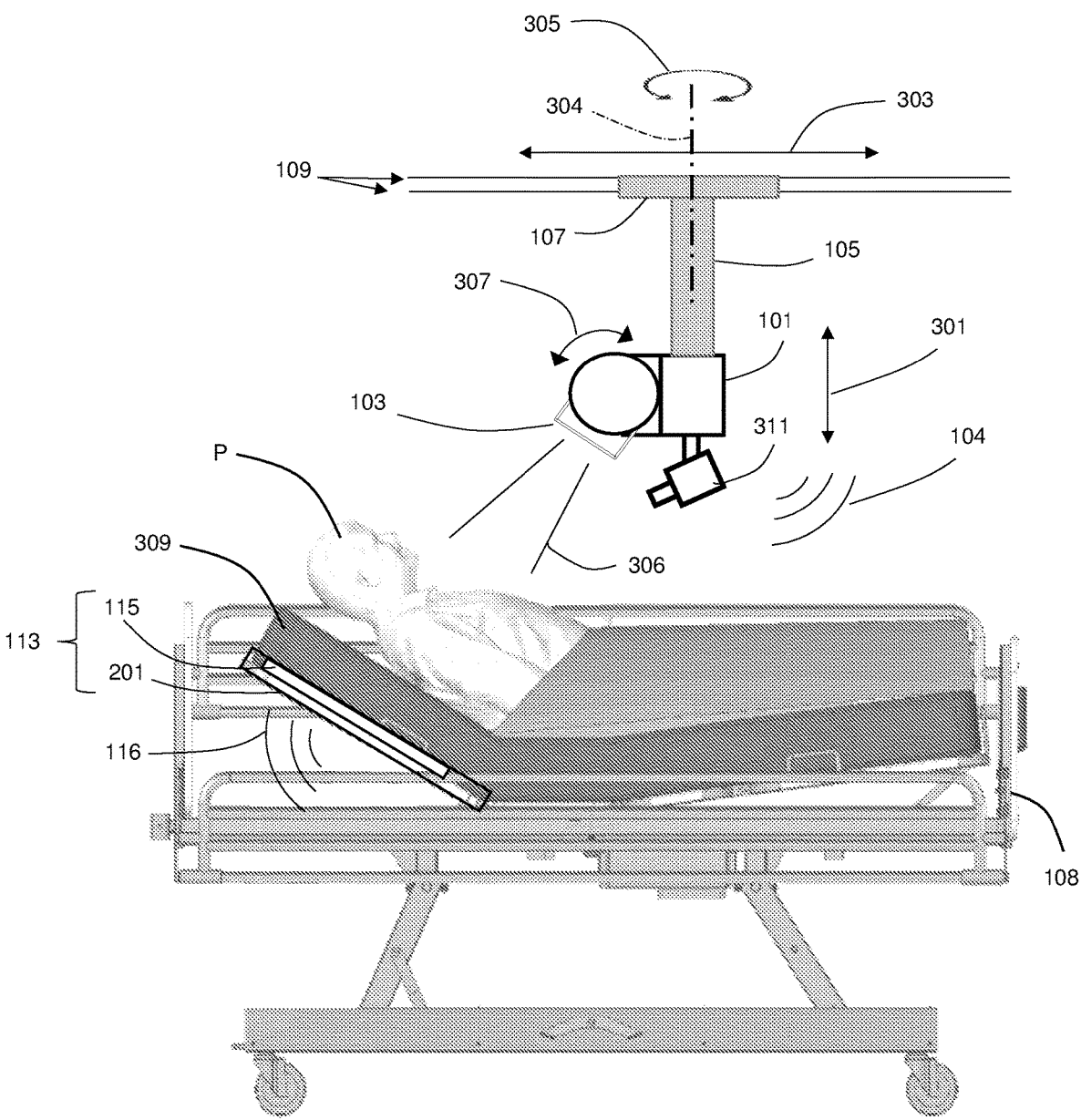
FIG. 3 is a side view of a patient being imaged using the exemplary radiographic imaging system of FIG. 1.

FIG. 1 and FIG. 3 illustrate an exemplary radiographic imaging system that may be deployed in medical imaging facilities such as in an ICU patient room 102. A movable tube head 101 includes an x-ray source, and has a collimator 103 attached thereto, which tube head 101 may be mounted on an overhead tube crane that includes an extendable vertical support column 105, to which the tube head 101 is attached, and a movable crane base 107, to which the extendable vertical support column 105 is attached. The movable crane base 107 is attached to crane tracks 109 which are affixed to a ceiling 111 of the patient room 102. When the crane base 107 is moved along the crane tracks 109, such as by a remote controllable motor drive, the tube head 101 may be moved to a desired position. The collimator 103 may include an electronically controlled collimator 103 having four individually movable blades for controlling a size of a rectangular aperture which, in turn, controls dimensions of an x-ray beam emitted by the x-ray source. The crane base 107 may also be be attached to second transverse tracks (not shown) to allow remote controlled movement of the tube head 101 along a transverse direction. Typically, the overhead tube crane movements may be configured to be perpendicular to each other and both parallel to a ceiling 111 of the room 102 containing the radiographic imaging system. The extendable vertical support column 105 may also be configured to be telescopically extendable and retractable vertically along directions 301 (FIG. 3). The crane base 107 includes an electric motor for controllably driving the crane base 107 along the tracks 109. Movement of the overhead tube crane allows controlled positioning of the tube head 101 in relation to the patient bed 108 and the DR detector 115 located therein. After controllably positioning the tube head 101 in relation to DR detector 115, for example, the x-ray source therewithin may be remotely and controllably fired to emit x-ray beam 306 (FIG. 3) to expose a patient lying on the patient bed 108 over the DR detector 115. As described in detail herein, such positioning of the tube head 101 and initiating x-ray exposures may be performed remotely without requiring personnel to be present in the ICU room 102. In one alternative embodiment, tube head 101 may include a plurality of x-ray sources such as carbon nanotubes or other cold cathode sources.

A user control console 130 may include a processing system 131 for remotely controlling operation of the radiographic imaging system described herein. The processing system 131 may include a wired coupling 139 or a wireless transmission capability via transceiver 137 for communicating with and controlling movement and operation of the overhead tube crane, the digital detector 115, a digital video camera 311 (FIG. 3), as well as the tube head 101 and the x-ray source(s) therein, such as a power level and/or firing sequence of the x-ray source(s), and timing of exposures to be captured by DR detector 115. The tube head 101 and digital camera 311 may include a wireless communication capability 104, and digital detector 115 and frame assembly 113 may also include wireless communication capability 116, respectively, for exchanging data and receiving commands and instructions from console 130. The control console 130 includes connected I/O devices such as a keyboard/mouse 135 and a digital display 133 for operator O use. The control console 130 may communicate wirelessly with DR detector 115 to transmit captured radiographic images to the control console 130, and for synchronizing an image capture sequence of the DR detector 115 with firing of the x-ray source(s) in tube head 101. The control console 130 may then transmit captured radiographic images to other network connected devices over a wired or wireless channel, such as to hand held tablets and cell phones. The control console 130 may be electronically connected to a medical facility communication network where the radiographic imaging system is installed.

The control console 130 may be located remotely from the patient room 102 to provide an environment for operator O that is isolated from the patient room 102. The control console 130 may be used by operator O to obtain radiographic images of a patient in patient room 102 without requiring operator O to have a direct line of sight of the patient P (FIG. 3) or the patient room 102. The control console 130 may be located in a control room of a medical facility on a different floor from the patient room 102, or even in a different building of the medical facility. If the medical facility network, which includes the control console 130, is connected to the internet then the control console 130 may be configured to be operable over the internet from hundreds of miles away, thereby allowing the radiography system disclosed herein to be used remotely by operators over large distances. In a separate embodiment, the control system 130 may be configured and located at a particular site so that operator O may have a line of sight view of the patient P and the patient bed 108, such as by providing a window through which the operator O can directly view the patient P. As will now be described in detail, the digital radiographic detector 115 is secured in a detector frame assembly 113 that is secured to the patient bed 108 and is configured to move the digital detector to a desired position within patient bed 108 while a patient is lying thereon.

With reference to the perspective view of FIG. 2A, detector frame assembly 113 includes a base frame 201 and a sub frame 203, both of which may be made from a substantially rigid planar material. Sub frame 203 includes a detector securing frame 205 attached thereto for holding the digital radiographic detector 115 therein. The planar base frame 201, planar sub frame 203, detector securing frame 205, and the detector 115 itself, may all be said to be disposed substantially parallel to each other. The sub frame 203 includes the following assembly configured to move the detector 115 along a y dimension. Detector securing frame 205 includes brackets 221a, 221b that are both slidably connected to y guide rod 223a, which is fixed to sub frame 203 in a position parallel to the y dimension. These brackets 221a, 221b, allow the detector securing frame 205 (as well as DR detector 115 therein) to move parallel to the y dimension by sliding along the y guide rod 223a. A control rod 227a is fixed to the bracket 221a and passes through electric motor & encoder 225a which is fixed to the sub frame 203. Electric motor & encoder 225a is configured to push and pull control rod 227a therethrough in order to drive bracket 221a further or closer along the y guide rod 223a. As the bracket 221a is driven back and forth along y guide rod 223a, the detector securing frame 205 and the DR detector 115 itself may be moved back and forth along the y dimension on the sub frame 203. Electric motor & encoder 225a is configured to measure, encode and transmit data to the processing system 131 that defines a precise distance that motor and encoder 225a pushes and/or pulls the control rod 227a so that a precise position of detector 115 in the y dimension may be determined by the processing system 131.

In a fashion similar, in certain respects, to the y dimension movement of the detector securing frame 205 just described, the sub frame 203 is configured to be moved in the x dimension that is perpendicular to the y dimension. The base frame 201 includes the following assembly configured to move the sub frame 203 in a x dimension. Sub frame 203 includes brackets 221c, 221d, that are both slidably connected to x guide rod 223, which is fixed to base frame 201 in a position parallel to the x dimension. These brackets 221c, 221d, allow the sub frame 203 (as well as the detector securing frame 205 and the DR detector 115 therein) to move parallel to the x dimension by sliding along the x guide rod 223. A control rod 227 is fixed to the bracket 221c and passes through electric motor & encoder 225 which is fixed to the base frame 201. Electric motor & encoder 225 is configured to push and pull control rod 227 therethrough in order to drive bracket 221c further or closer along the x guide rod 223. As the bracket 221c is driven back and forth along x guide rod 223, the sub frame 203, the detector securing frame 205 and the DR detector 115 itself may be moved back and forth along the x dimension on the base frame 201. Electric motor & encoder 225 is configured to measure, encode and transmit data to the processing system 131 defining a precise distance that motor and encoder 225 pushes and/or pulls the control rod 227 so that a precise position of detector 115 in the x dimension may be determined by the processing system 131. Thus, the digital detector 115 may be defined as being selectively movable in a plane occupied by the detector, which detector plane is substantially parallel to a plane of the base frame 201 and a plane of the sub frame 203.

FIGS. 2B-2E illustrate top views of exemplary terminal positions of the detector 115 in the x-y dimensions, with a portion of the frame assembly 113 elements enumerated in FIG. 2C for clarity. FIG. 2B illustrates the detector 115 moved to a position in a maximum x dimension (furthest right) and minimum y dimension (furthest downward) illustrated by the arrows adjacent FIG. 2B. FIG. 2C illustrates the detector 115 moved to a position in a minimum x dimension (furthest left) and minimum y dimension (furthest downward) illustrated by the arrows adjacent FIG. 2C. FIG. 2D illustrates the detector 115 moved to a position in a minimum x dimension (furthest left) and maximum y dimension (furthest upward) illustrated by the arrows adjacent FIG. 2D. FIG. 2E illustrates the detector 115 moved to a position in a maximum x dimension (furthest right) and a maximum y dimension (furthest upward) illustrated by the arrows adjacent FIG. 2E.

FIG. 3 illustrates a side view of the radiographic imaging system of FIG. 1, described herein above, in operation having a patient P to be radiographically imaged while lying on patient bed 108. As shown in FIG. 3, and partially described with reference to FIG. 1 herein, tube head 101, having an x-ray source, or sources, therein and a collimator 103 attached thereto, is mounted on extendible vertical support column 105 which, in turn, is attached to crane base 107 that is configured to move along crane tracks 109 mounted on a ceiling 111 of patient room 102. Alternatively, the tube head 101 containing an x-ray source and collimator 103 may be mounted on a wall of the patient room 102. The tube head 101 may be: (a) moved vertically in directions 301 using telescoping extendible vertical support column 105; (b) moved horizontally in directions 303 using crane base 107 movement along crane tracks 109; and (c) rotated about vertical axis 304 in directions 305. Similarly, tube head 101 and collimator 103 may be rotated in directions 307 to emit an x-ray beam 306 at a desired angle. The tube head 101 may be positioned so as to align the x-ray beam 306 with the DR detector 115, positioned in the frame assembly 113 within patient bed 108 having a radiolucent patient cushion 309 placed thereon for patient P comfort.

As shown in FIG. 3, a patient P may be lying on an ICU room bed 108 having a DR detector 115 positioned therewithin as described herein. A tube head 101 having an x-ray source is controllably positioned by an operator O using control console 130 as described herein. To properly position the tube head 101 and the detector 115, the operator O may make use of a live video digital camera 311 attached, for example, to tube head 101 and aimed at patient P. The video camera 311 may capture and transmit a live video image of the patient P for display to an operator O on digital display 133 (see, e.g., FIG. 4). Fiducial markers 121 (FIGS. 1 and 4) may be positioned on patient bed 108, and recognized by programmed digital recognition at console processing system 131 by analyzing the live video image of the fiducial markers 121 displayed on the digital display 133. Together with encoder data transmitted by encoder 225 identifying a current x position of the detector 115 and encoder data transmitted by encoder 225a identifying a current y position of detector 115, processing system 131 may be programmed to precisely calculate an x-y position of detector 115 in the frame assembly 113. To initialize the detector 115 x-y position, the initial location of the detector 115 relative to fiducial markers 121 may be recorded as x1 and y1 (FIG. 1) in processing system 131. Further x-y dimensional movement of the detector 115 within frame assembly 113, as identified by data transmitted from electric motor and encoders 225, 225a, are also updated and stored in processing system 131. The fiducial markers 121 may be positioned in locations having known fixed x-y displacements relative to the base frame 201 and the detector 115 positioned therein. Thus, calculating a current x-y position of the detector 115 is achieved using the fiducial markers 121, as displayed in the digital display 133, and the received encoder data.

Figure 4:
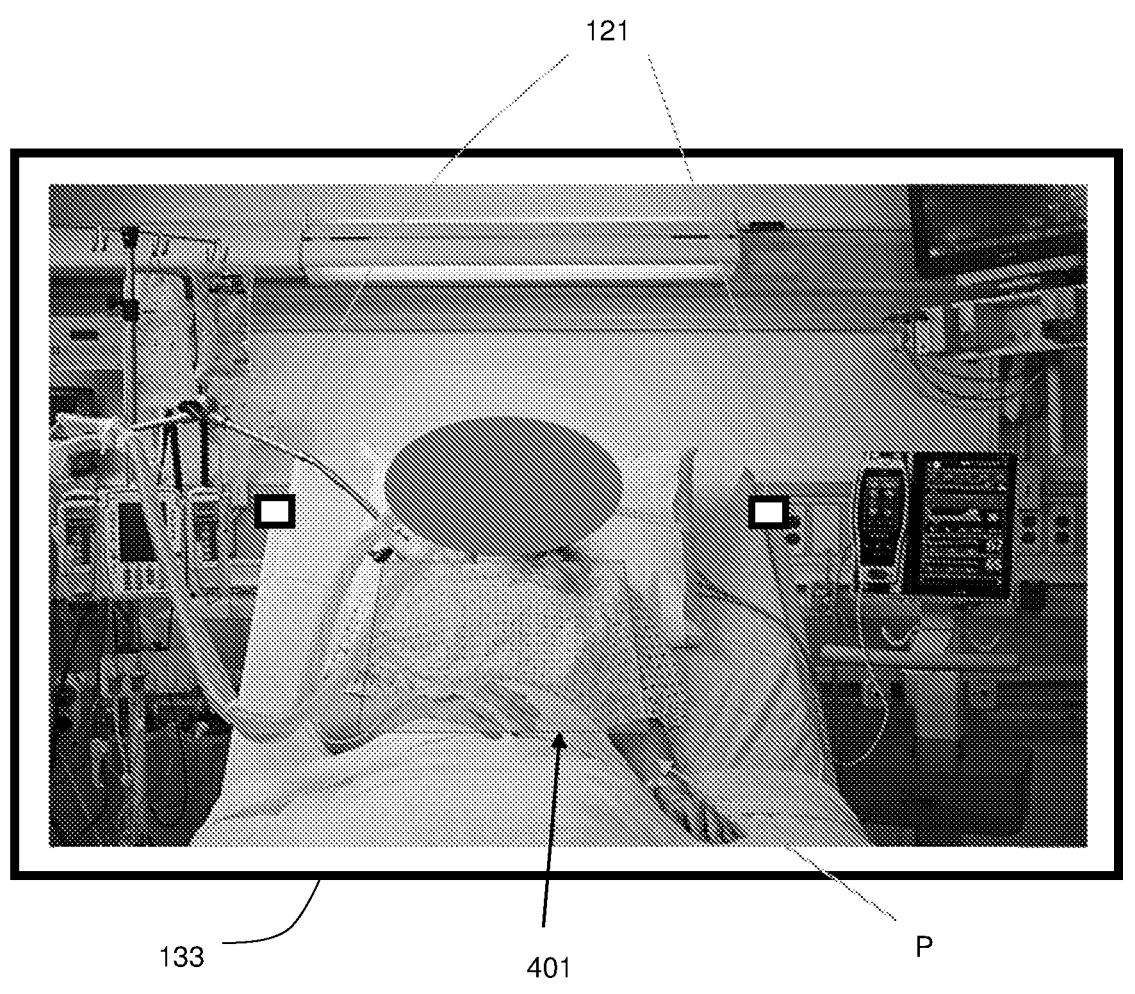
FIG. 4 is a view of a digital display connected to the radiographic imaging system of the present invention.

With reference to FIG. 4, based on a calculation of the current position of detector 115, as it is selectively moved in the frame assembly 113, processing system 131 may be configured to overlay a movable semi-transparent cursor 401, resembling and representing a rectangular shape of the detector 115, on the digital display 133 to indicate an actual current position of the detector 115 to an operator O. Based on the displayed cursor 401 position, the operator O may further selectively adjust the position of the detector 115 within the frame assembly 113 until the detector 115 is in a satisfactory position for initiating a radiographic image capture of patient P as indicated by the cursor 401. Thus, the position of the detector 115 as illustrated by the rectangular cursor 401 overlaying the live video image of the patient P may be used by the operator O to verify accurate detector 115 placement.

The control console 130 may be configured to transmit wireless control signals using transceiver 137, in response to operator O instructions input to the control console 130 to synchronize image capture timing in the detector 115 and to receive radiographic images captured and transmitted by the detector 115. Similarly, the control console 130 may be configured to transmit control signals to frame assembly 113 to move the detector 115 along x-y dimensions, as desired, and to tube head 101 to control power levels and to activate firing of the x-ray source(s). The control console 130 may also be configured to transmit wireless control signals to control rotational and extension movement of the extendible vertical support column 105 and motorized crane base 107 along crane tracks 109. The control console 130 may receive instructions and commands from an operator O inputting requests via a keyboard or mouse 135, for example. In one embodiment, the video camera 311 may be attached to the patient bed 108 or it may be attached to another structure in a room 102 of a medical facility treating the patient P.

Portions of the radiographic imaging system described herein having remote controllable movement may each include a motor that is wirelessly controllable to rotate, extend/retract, or move along guides or tracks. Positioning of the tube head 101 allows accurate positioning of the x-ray source(s) therewithin in relation to the DR detector 115 and patient P. After controllably positioning the tube head 101 in relation to DR detector 115 and patient P, for example, the x-ray source therewithin may be remotely and controllably fired to emit an x-ray beam 306 to expose patient P and capture a radiographic image thereof in DR detector 115. As further described in detail herein, such positioning and radiographic image capture may be performed remotely without requiring personnel to be present in the ICU room 102.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The inventionm claimed is:

1. A radiography imaging system comprising:
a bed having a surface for supporting a patient;
a tube head including an x-ray source for radiographically exposing the patient supported by the bed, the tube head electrically connected to a control console operated by an operator;
a frame attached to the bed under the surface, the frame comprising a component support to hold a digital radiographic detector, the frame configured to move the component support to a desired location within the frame in response to communications input by the operator at the control console;
a plurality of fiducial markers disposed on the bed at predetermined distances from the frame;
a digital camera aimed at the patient and configured to display a video image of the fiducial markers and of the patient supported by the bed on a digital display.

2. The system of claim 1, wherein the component support comprises a digital radiographic detector, the digital radiographic detector attached to the component support.

3. The system of claim 2, further comprising two perpendicular guides attached to the frame each for guiding the component support during movement of the component support within the frame.

4. The system of claim 3, further comprising an encoder attached to the frame to transmit encoder data to the control console, the encoder data indicating a position of the component support within the frame.

5. The system of claim 4, further comprising a processing system at the control console configured to calculate a position of the digital radiographic detector with respect to the bed based on the transmitted encoder data and on the position of the fiducial markers displayed on the digital display, and configured to generate and display a graphic overlay on the displayed captured image of the patient, the graphic overlay selectively positioned on the digital display, based on the calculated position, to indicate a location of the digital radiographic detector with respect to the patient.

6. A method comprising:
providing a bed having a surface for supporting a patient;
attaching a controllably moveable frame assembly to the bed under the surface;
attaching a digital radiographic detector to the frame assembly;
attaching a tube head having an x-ray source above the bed and aimed at the patient supported by the bed, including attaching a video camera to the tube head and displaying the patient supported by the bed on a digital display;
attaching the tube head to a control console operated by an operator, including providing controls at the control console for the operator to controllably move the frame assembly to a desired position; and
the operator moving the digital radiographic detector in a x-y plane of the detector under the surface of the bed to the desired location using the controls at the control console and determining the desired position by viewing the digital display.

7. The method of claim 6, wherein the step of the operator moving the digital radiographic detector includes displaying a graphic representation of a position of the detector on the digital display overlaid on a live video image of the patient.

8. The method of claim 7, wherein the step of the operator moving the digital radiographic detector includes moving the digital radiographic detector in one or both of two perpendicular directions in the x-y plane.

9. The method of claim 8, further comprising transmitting data representing a magnitude of movement of the digital radiographic detector in said one or both of the two perpendicular directions.

10. The method of claim 9, further comprising determining a position of the detector using the data representing the magnitude of movement of the digital radiographic detector.

11. The method of claim 10, further comprising using the determined position of the detector to display the graphic representation of the position of the detector overlaid on a corresponding position of the live video image of the patient.

12. The method of claim 11, further comprising attaching at least two fiducial markers on the bed at predetermined distances from the frame assembly and displaying the fiducial markers on the digital display.

13. A radiography imaging system comprising:
a bed having a surface for supporting a patient;

a tube head including an x-ray source for radiographically exposing the patient supported by the bed;

a control console communicatively connected to the tube head and operated by an operator, the control console including a digital screen for displaying video images;

a video digital camera attached to the tube head and connected to the control console, the digital screen configured to display a video image of the patient supported by the bed; and a frame attached to the bed under the surface, the frame comprising a component support to hold a digital radiographic detector, the frame configured to move the component support to a desired location within the frame in response to an operator operating the control console while viewing the digital screen displaying the patient supported by the bed.

14. The system of claim 13, further comprising a plurality of fiducial markers attached to the bed and displayed on the digital screen, wherein the digital screen is configured to display a cursor outlining a current position of the digital radiographic detector in relation to the patient based on positions of the displayed fiducial markers, the fiducial markers positioned at predetermined distances in relation to the frame, and wherein a current position of the cursor on the display is determined by the positions of the displayed fiducial markers.

15. The system of claim 14, wherein the tube head is configured to be selectively moved to a radiographic imaging position by the human operator viewing the digital screen at the control console, and wherein the x-ray source is configured to be activated by the operator at the control console for radiographically imaging the patient.

16. The system of claim 15, wherein the control console is provided at a location remote from the patient bed.

17. The system of claim 13, wherein the frame comprises two perpendicular guides attached to the frame and each configured to guide the component support during movement of the component support within the frame.

* * * * *